US008454905B2

(12) United States Patent
Pope et al.

(10) Patent No.: US 8,454,905 B2
(45) Date of Patent: Jun. 4, 2013

(54) DROPLET ACTUATOR STRUCTURES

(75) Inventors: Lavern Pope, Raleigh, NC (US); Michael G. Pollack, Durham, NC (US); Vamsee K. Pamula, Durham, NC (US)

(73) Assignee: Advanced Liquid Logic Inc., Research Triangle Park, NC (US)

( * ) Notice: Subject to any disclaimer, the term of this patent is extended or adjusted under 35 U.S.C. 154(b) by 0 days.

(21) Appl. No.: 12/681,840

(22) PCT Filed: Oct. 17, 2008

(86) PCT No.: PCT/US2008/080275
§ 371 (c)(1), (2), (4) Date: Apr. 14, 2010

(87) PCT Pub. No.: WO2009/052354
PCT Pub. Date: Apr. 23, 2009

(65) Prior Publication Data

US 2010/0236927 A1 Sep. 23, 2010

Related U.S. Application Data

(60) Provisional application No. 60/980,724, filed on Oct. 17, 2007.

(51) Int. Cl.
*G01N 15/06* (2006.01)
*G01N 33/00* (2006.01)
*G01N 33/48* (2006.01)

(52) U.S. Cl.
USPC ............ 422/504; 422/50; 422/68.1; 422/502; 422/503; 436/43; 436/174; 436/180

(58) Field of Classification Search
USPC ............... 422/50, 68.1, 502, 504, 82; 436/43, 436/174, 180
See application file for complete search history.

(56) References Cited

U.S. PATENT DOCUMENTS

| | | | | |
|---|---|---|---|---|
| 6,565,727 | B1 * | 5/2003 | Shenderov | 204/600 |
| 6,773,566 | B2 * | 8/2004 | Shenderov | 204/450 |
| 6,790,011 | B1 | 9/2004 | Le Pesant | |
| 6,911,132 | B2 * | 6/2005 | Pamula et al. | 204/600 |

(Continued)

FOREIGN PATENT DOCUMENTS

| | | | |
|---|---|---|---|
| JP | 2006-276801 | A | 10/2006 |
| WO | 2007120241 | A2 | 10/2007 |

(Continued)

OTHER PUBLICATIONS

B. Berge et al. ("Variable focal lens controlled by an external voltage: An application of electrowetting," Eur. Phys. J. E 3, pp. 159-163 (2000).*

(Continued)

*Primary Examiner* — Brian J Sines
(74) *Attorney, Agent, or Firm* — William A. Barrett; Ward and Smith, P.A.

(57) ABSTRACT

A droplet actuator comprising a substrate comprising an electrode coupled to a voltage source, wherein the droplet actuator is configured such that when voltage is applied to the electrode, an electrostatic energy gradient is established at a surface of the substrate which causes a droplet to be transported in a direction established by the energy gradient. Related methods and other embodiments are also provided.

20 Claims, 3 Drawing Sheets

U.S. PATENT DOCUMENTS

Figure 1:
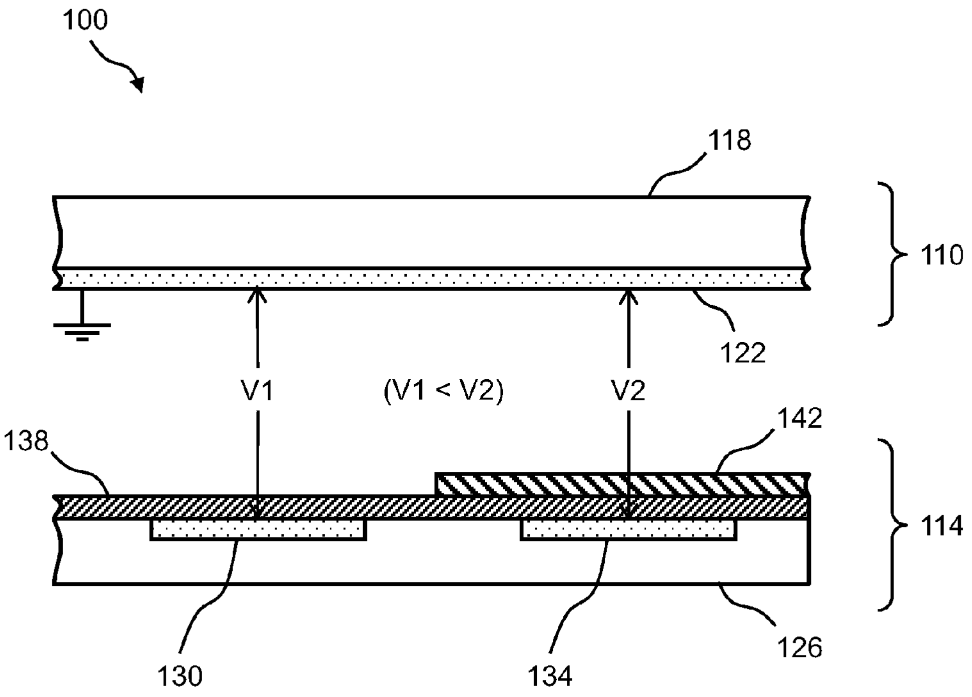

| | | | |
|---|---|---|---|
| 6,958,132 B2 | 10/2005 | Chiou et al. | |
| 7,255,780 B2 | 8/2007 | Shenderov | |
| 7,569,129 B2 | 8/2009 | Pamula | |
| 7,943,030 B2 | 5/2011 | Shenderov | |
| 8,128,798 B2 | 3/2012 | Adachi | |
| 8,221,605 B2 | 7/2012 | Pollack | |
| 2005/0260686 A1 | 11/2005 | Watkins et al. | |
| 2006/0194331 A1 | 8/2006 | Pamula et al. | |
| 2006/0260919 A1* | 11/2006 | Aimi et al. | 200/83 F |
| 2008/0053205 A1 | 3/2008 | Pollack et al. | |
| 2008/0169195 A1* | 7/2008 | Jones et al. | 204/547 |

FOREIGN PATENT DOCUMENTS

| | | |
|---|---|---|
| WO | 2007123908 A2 | 11/2007 |
| WO | 2008098236 A2 | 8/2008 |
| WO | 2008116221 A1 | 9/2008 |
| WO | 2008134153 A1 | 11/2008 |
| WO | 2009021173 A1 | 2/2009 |

OTHER PUBLICATIONS

B. Berge ("Liquid Lens Technology" Principle of Electrowetting Based Lenses and Applications to Imaging, IEEE (2005).*

Jie Ding, "System level architectural optimization of semi-reconfigurable microfluidic system," M.S. Thesis, Duke University Dept of Electrical Engineering, 2000.

Lee J, Moon H, Fowler J, et al., "Electrowetting and electrowetting-on-dielectric for microscale liquid handling," Sensors and Actuators A—Physical, vol. 95 (2-3): pp. 259-268, Jan. 1, 2002.

Hyejin Moon, "Electrowetting-On-Dielectric Microfluidics: Modeling, Physics, and MALDI Application," Ph.D. Dissertation, University of California Dept. of Mechanical Engineering, published Aug. 2006.

H. Ren, R. B. Fair, M. G. Pollack, and E. J. Shaughnessy, "Dynamics of electro-wetting droplet transport," Sensors and Actuators B (Chemical), vol. B87, No. 1, pp. 201-206, Nov. 15, 2002.

Srinivasan, Vijay, "A Digital Microfluidic Lab-on-a-Chip for Clinical Diagnostic Applications," Doctoral Thesis—Department of Electrical and Computer Engineering, Duke University, 2005.

Pollack, Michael, "Electrowetting-Based Microactuation of Droplets for Digital Microfluidics," Doctoral Thesis, Department of Electrical and Computer Engineering—Duke University, 2001.

Pamula et al, U.S. Appl. No. 61/047,789, "Droplet Actuator Devices and Droplet Operations Using Beads," filed Apr. 25, 2008.

Sista et al., U.S. Appl. No. 61/039,183, "Multiplexing Bead Detection in a Single Droplet," filed Mar. 25, 2008.

Pamula et al., U.S. Appl. No. 61/086,183, "Droplet Actuator Devices and Methods for Manipulating Beads," filed Aug. 5, 2008.

* cited by examiner

DROPLET ACTUATOR STRUCTURES

RELATED APPLICATIONS

This application claims priority to U.S. patent application Ser. No. 60/980,724, entitled "Droplet actuator structures with varied substrate thickness," filed on Oct. 17, 2007, the entire disclosure of which is incorporated herein by reference.

BACKGROUND

Droplet actuators are used to conduct a wide variety of droplet operations. A droplet actuator typically includes two substrates separated by a gap. The substrates include electrodes for conducting droplet operations. The gap between the substrates is typically filled with a filler fluid that is immiscible with the fluid that is to be subjected to droplet operations. Droplet operations are controlled by electrodes associated with one or both of the substrates. As the number of electrodes in droplet actuators increases, there is a need for alternative approaches to providing control interaction of fields produced by electrodes with droplets.

SUMMARY OF THE INVENTION

The invention provides a droplet actuator. The droplet actuator includes a substrate with an electrode coupled to a voltage source. The droplet actuator may be configured such that when voltage is applied to the electrode, an electrostatic energy gradient is established at a surface of the substrate which is sufficient to cause a droplet on or in proximity to the electrode to be transported in a direction established by the energy gradient. The electrode may be a two terminal electrode composed of a resistive material, such that the electrode functions as a resistor with a spatial distribution of electric potential along its length.

The droplet actuator may in some cases be coupled to a second voltage source; and configured such that when voltage to the first and second voltage sources, an electrostatic energy gradient is established at a surface of the substrate which causes a droplet to be transported in a direction established by the energy gradient.

In certain embodiments, the electrostatic energy gradient at the surface of the substrate is established by a voltage difference between the first and second voltage sources. For example, the voltage difference may range from about >0 volts to about 300 volts.

In certain embodiments, the electrostatic energy gradient results from a gradient in thickness of a material layered above the electrode. For example, the electrostatic energy gradient may result from a difference in thickness of a dielectric material layered above the electrode. Similarly, the electrostatic energy gradient may result from a gradient in dielectric constant of one or more dielectric materials layered above the electrode. Moreover, the electrostatic energy gradient may result from a gradient in distance of the electrode's surface from the substrate's surface.

In some embodiments, the electrostatic energy gradient is continuous. In other embodiments, the electrostatic energy gradient is discontinuous (see FIG. 1, bracket labeled A).

The invention also provides a method of transporting a droplet. The method may make use of a droplet actuator of the invention. Applying voltage to the electrode will cause the droplet to be transported in a direction established by the energy gradient.

In certain embodiments, the droplet may include one or more beads. The beads may be magnetically responsive beads. The beads may be substantially non-magnetically responsive beads. The droplets may include one or more pre-selected biological cells.

The invention also provides a droplet actuator comprising: a substrate; an electrode path associated with the substrate; a dielectric layer overlying the electrode, wherein: the dielectric layer has a thickness; and comprises region in which the thickness varies.

The region may overly a single electrode of the electrode path. The region may overly two or more electrodes of the electrode path. The region may lie generally between two electrodes of the electrode path.

In certain embodiments droplet actuator substrate includes at least two zones of generally uniform thickness separated by the segment. In other embodiments droplet actuator substrate includes at least three zones of generally uniform thickness separated by the segment.

DEFINITIONS

As used herein, the following terms have the meanings indicated.

"Activate" with reference to one or more electrodes means effecting a change in the electrical state of the one or more electrodes which, in the presence of a droplet, results in a droplet operation.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical and other three dimensional shapes. The bead may, for example, be capable of being transported in a droplet on a droplet actuator or otherwise configured with respect to a droplet actuator in a manner which permits a droplet on the droplet actuator to be brought into contact with the bead, on the droplet actuator and/or off the droplet actuator. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead or one component only of a bead. The remainder of the bead may include, among other things, polymeric material, coatings, and moieties which permit attachment of an assay reagent. Examples of suitable magnetically responsive beads are described in U.S. Patent Publication No. 2005-0260686, entitled, "Multiplex flow assays preferably with magnetic particles as solid phase," published on Nov. 24, 2005, the entire disclosure of which is incorporated herein by reference for its teaching concerning magnetically responsive materials and beads. The fluids may include one or more magnetically responsive and/or non-magnetically responsive beads. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. patent application Ser. No. 61/039,183, entitled "Multiplexing Bead Detection in a Single Droplet," filed on Mar. 25, 2008; U.S. patent application Ser. No. 61/047,789, entitled "Droplet Actuator Devices and Droplet Operations Using Beads," filed on Apr. 25, 2008; U.S. patent application Ser. No. 61/086,183, entitled "Droplet Actuator Devices and Methods for Manipulating Beads,"

filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see U.S. Pat. No. 6,911,132, entitled "Apparatus for Manipulating Droplets by Electrowetting-Based Techniques," issued on Jun. 28, 2005 to Pamula et al.; U.S. patent application Ser. No. 11/343,284, entitled "Apparatuses and Methods for Manipulating Droplets on a Printed Circuit Board," filed on filed on Jan. 30, 2006; U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000, both to Shenderov et al.; Pollack et al., International Patent Application No. PCT/US2006/047486, entitled "Droplet-Based Biochemistry," filed on Dec. 11, 2006, the disclosures of which are incorporated herein by reference. Methods of the invention may be executed using droplet actuator systems, e.g., as described in International Patent Application No. PCT/US2007/009379, entitled "Droplet manipulation systems," filed on May 9, 2007. In various embodiments, the manipulation of droplets by a droplet actuator may be electrode mediated, e.g., electrowetting mediated or dielectrophoresis mediated.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; condensing a droplet from a vapor; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. In various embodiments, the droplet operations may be electrode mediated, e.g., electrowetting mediated or dielectrophoresis mediated. Other examples of techniques for effecting droplet operations include opto-electrowetting, optical tweezers, surface acoustic waves, thermocapillary-driven droplet motion, chemical surface energy gradients, and pressure or vacuum induced droplet motion.

"Filler fluid" means a fluid associated with a droplet operations substrate of a droplet actuator, which fluid is sufficiently immiscible with a droplet phase to render the droplet phase subject to electrode-mediated droplet operations. The filler fluid may, for example, be a low-viscosity oil, such as silicone oil. Other examples of filler fluids are provided in International Patent Application No. PCT/US2006/047486, entitled, "Droplet-Based Biochemistry," filed on Dec. 11, 2006; and in International Patent Application No. PCT/US2008/072604, entitled "Use of additives for enhancing droplet actuation," filed on Aug. 8, 2008.

"Immobilize" with respect to magnetically responsive beads, means that the beads are substantially restrained in position in a droplet or in filler fluid on a droplet actuator. For example, in one embodiment, immobilized beads are sufficiently restrained in position to permit execution of a splitting operation on a droplet, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

The terms "top" and "bottom" are used throughout the description with reference to the top and bottom substrates of the droplet actuator for convenience only, since the droplet actuator is functional regardless of its position in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

DESCRIPTION

The invention provides nonlimiting examples of single metal layer structures for droplet actuators that, among other things, include various dielectric layer configurations for minimizing the number of controls in order to help mitigate wireability constraints and/or the limited droplet manipulation mechanisms. In particular, the invention provides single-layer layouts for generating multiple electrostatic energy levels or an electrostatic energy gradient from a single voltage source by use of combinations of various dielectric layer configurations atop the electrodes. In doing so, the number of controls for performing droplet operations in a single-layer wiring design is minimized.

5.1 Example Dielectric Layer Configurations

FIG. 1 illustrates a side view of a droplet actuator layout 100 that includes a nonlimiting example of a dielectric layer configuration that uses two electrowetting voltages that may be supplied by a single voltage source for conducting droplet operations. Droplet actuator 100 includes a first plate, such as a top plate 110, and a second plate, such as a bottom plate 114. Top plate 110 may be formed of a substrate 118, upon which is disposed a ground electrode 122. Bottom plate 114 may be formed of a substrate 126, upon which is disposed a first electrode 130 and a second electrode 134. Atop the substrate 126 is disposed a first dielectric layer 138, which covers both first electrode 130 and second electrode 134. A second dielectric layer 142 is disposed atop first dielectric layer 138 in, for example, the area of second electrode 134 only, as shown in FIG. 1. First dielectric layer 138 and second dielectric layer 142 may be formed of any dielectric material, such as polyimide. Top plate 110 and bottom plate 114 are arranged one to another such that there is a gap therebetween that provides a fluid flow path for conducting droplet operations.

In one example, first electrode 130 is representative of one of a plurality of transport electrodes that provide a certain electrostatic energy level that is generated via an electrowetting voltage V1, which is a function of a single layer of dielectric, such as first dielectric layer 138. Likewise, second electrode 134 is representative of one of a plurality of transport electrodes that provide a certain electrostatic energy level that is generated via an electrowetting voltage V2, which is a function of two layers of dielectric, such as the combination of first dielectric layer 138 and second dielectric layer 142. Consequently, in order to provide the required electrostatic energy levels, the minimum electrowetting voltage V2 at second electrode 134 is greater than the minimum electrowetting voltage V1 at first electrode 130. In one example, the minimum electrowetting voltage V1 may be from about 95 volts to about 110 volts and the minimum electrowetting voltage V2 may be from about 134 volts to about 155 volts. The electrowetting voltages V1 and V2 may be supplied by a common voltage source or, alternatively, from separate voltages sources.

In operation, a certain electrowetting voltage V1 is applied and an electrowetting process is performed at the single-layer dielectric portion of droplet actuator layout 100, such as at first electrode 130. Subsequently, a certain electrowetting voltage V2, which is higher than electrowetting voltage V1, is applied and the electrowetting process may be performed at both the single-layer dielectric portion of droplet actuator layout 100, such as at first electrode 130, and the two-layer dielectric portion of droplet actuator layout 100, such as at second electrode 134. A droplet (not shown) may be manipulated back and forth between the low-voltage and high-voltage regions, depending on the process requirements.

In one example application, a first set of reagents may be manipulated at a certain electrowetting voltage V1 for which it is optimized and a second set of reagents may be manipulated at a certain higher electrowetting voltage V2 for which it is optimized In this way, droplet actuator layout 100 may be utilized with two sets of reagents while operating with a single voltage source. In another example application, a reagent that has been deteriorated or otherwise affected by a certain electrowetting voltage V2 at the high-voltage region may be subsequently usable in the low-voltage region of electrowetting voltage V1.

Figure 2:
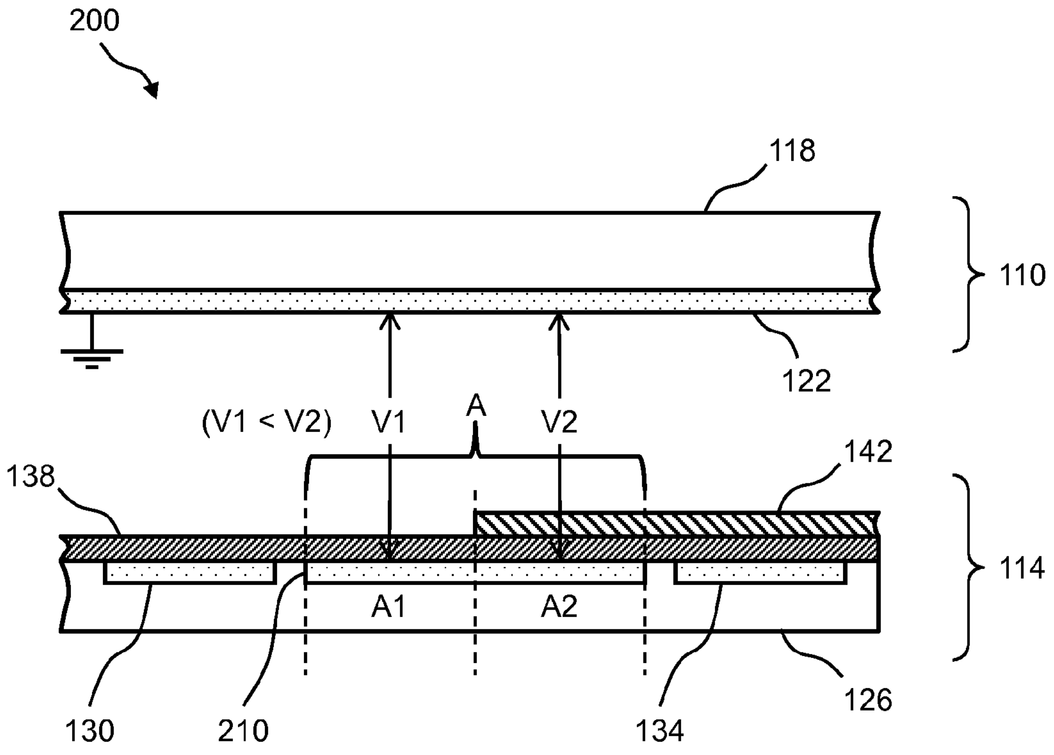

FIG. 2 illustrates a side view of a droplet actuator layout 200 that includes another nonlimiting example of a dielectric layer configuration that uses two electrowetting voltages that may be supplied by a single voltage source for conducting droplet operations. Droplet actuator 200 is substantially the same as droplet actuator layout 100 of FIG. 1, except that bottom plate 114 of droplet actuator layout 200 further includes an electrode 210 that has a first area A1 that is covered with one dielectric layer and a second area A2 that is covered with two dielectric layers. More specifically, FIG. 2 shows electrode 210 that may have a length of, for example, 2 times the length of first electrode 130 and second electrode 134, such that its first area A1 is covered with first dielectric layer 138 only and its second area A2 is covered with both first dielectric layer 138 and second dielectric layer 142. As a result, the electrowetting voltage V1 is associated with first area A1 of electrode 210 and the electrowetting voltage V2 is associated with second area A2 of electrode 210. A droplet (not shown) may be manipulated across electrode 210 between the low- and high-voltage regions.

Figure 3:
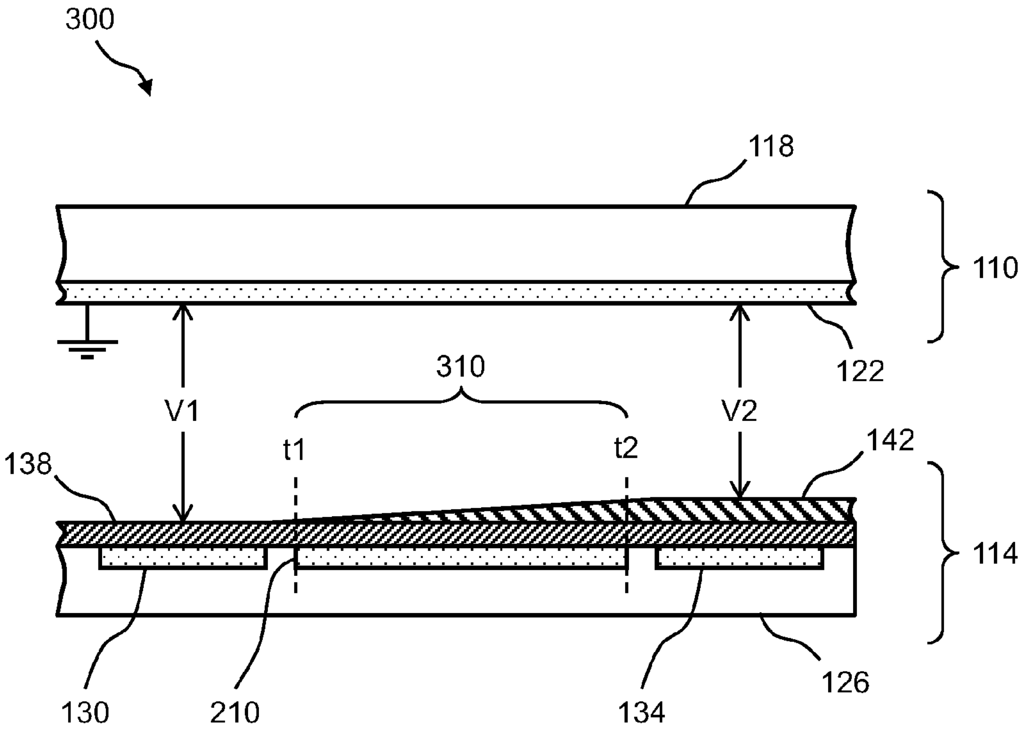

FIG. 3 illustrates a side view of a droplet actuator layout 300 that includes a nonlimiting example of a dielectric layer configuration that uses a dielectric layer thickness gradient to control electrostatic energy for conducting droplet operations. Droplet actuator 300 is substantially the same as droplet actuator layout 200 of FIG. 2, except that second dielectric layer 142 spans the full length of electrode 210 and, in particular, second dielectric layer 142 includes a tapered region 310 that spans electrode 210, as shown in FIG. 3. Within tapered region 310, second dielectric layer 142 has a thickness t1 at one edge of electrode 210 and a thickness t2 at the opposite edge of electrode 210. In one example, t2 is about 2 times t1.

In operation, regardless of whether electrowetting voltage V1 or V2 is applied, an electrostatic energy gradient is formed, for example, across electrode 210 as a result of the dielectric layer thickness gradient of second dielectric layer 142 at tapered region 310. Consequently, for any electrowetting voltage V1 or V2, the electrostatic energy at t1 of tapered region 310 is greater than the electrostatic energy at t2. The resulting electrostatic energy gradient across electrode 210 may be used for controlling the movement of a droplet (not shown) across electrode 210 when conducting droplet operations.

The dielectric layer configurations of droplet actuator layouts 100, 200, and 300 of FIGS. 1, 2, and 3, respectively, are not limited to one and two dielectric layers only. Any number and combinations of numbers of dielectric layers and respective electrowetting voltages is possible.

The invention allows for multiplexing of electrodes in which a voltage increase is required to effect droplet operations on the regions of the droplet actuator with a thicker layer separating the droplet from the electrode. For example, consider an embodiment in which a droplet actuator has two thicknesses of substrate materials and where certain electrodes in both regions are coupled to a common switch and thus activated at the same time. A dispensing operation using the low voltage setting will result in dispensing only in the portion of the droplet actuator with the thinner substrate. However, a dispensing operation at the high voltage setting may result in dispensing of droplets on both sides of the substrate.

Moreover, a droplet on the thinner region may be manipulated alongside an activated electrode in the thicker region, but the droplet will not be transported to the thicker region unless the higher voltage is used to an electrode in the thicker region that is sufficiently proximate to the droplet to cause the droplet to be transported onto the thicker region.

It should be noted that in embodiments in which there is a gap height difference between the thicker and thinner region, the droplet will have a tendency to settle in the region with the larger gap height. To transport a droplet into the thicker region, the voltage may be adjusted to overcome this tendency. In other droplets, the droplet operations surface may be level across different regions, and the difference in thickness may be established by manufacturing the electrodes at different depths relative to the droplet operations surface.

The invention includes embodiments in which there are multiple regions having different substrate thicknesses. For example, in one embodiment, the droplet actuator has two substrate thicknesses and multiple areas of each thickness. In another example, the droplet actuator as multiple areas of different substrate thicknesses that collectively include and 2, 3, 4, 5 or more substrate thicknesses.

The invention also provides a droplet actuator comprising a substrate comprising an electrode coupled to a voltage source, wherein the droplet actuator is configured such that when voltage is applied to the electrode, an electrostatic energy gradient is established at a surface of the substrate which causes a droplet to be transported in a direction established by the energy gradient.

The electrode may, for example, be a two terminal electrode composed of a resistive material, such that the electrode functions as a resistor with a spatial distribution of electric potential along its length. The electrode may also be coupled to a second voltage source and configured such that when voltage to the first and second voltage sources, an electrostatic energy gradient is established at a surface of the substrate which causes a droplet to be transported in a direction established by the energy gradient.

In various embodiments, the electrostatic energy gradient at the surface of the substrate may be established by a voltage difference between the first and second voltage sources. For example, the voltage difference ranges from about >0 volts to about 300 volts. The electrostatic energy gradient may, in various embodiments, result from a gradient in thickness of a material layered above the electrode. The electrostatic energy gradient may, in various embodiments, result from a difference in thickness of a dielectric material layered above the electrode. The electrostatic energy gradient may, in various embodiments, result from a gradient in dielectric constant of a dielectric material layered above the electrode. The electrostatic energy gradient may, in various embodiments, result from a gradient in distance of the electrode's surface from the substrate's surface. The electrostatic energy gradient may vary in a continuous or discontinuous manner.

Droplet operations effected by the electrostatic energy gradient are within the scope of the invention, e.g., applying voltage to the electrode and thereby causing the droplet to be transported in a direction established by the energy gradient. For example, the invention provides a method of transporting a droplet, the method comprising: (a) providing a droplet actuator comprising a substrate comprising: (i) a droplet operations surface; (ii) an electrode associated with the substrate, coupled to a voltage source, and configured such that when voltage is applied to the electrode, an electrostatic energy gradient is established at the droplet operations surface; (b) providing a droplet on the droplet operations surface; (c) applying voltage to the electrode and thereby causing the droplet to be transported in a direction established by the energy gradient.

One approach for minimizing the number of controls in a single metal layer designs for droplet actuators may include, but is not limited to, the steps of (1) providing a first region that has a first dielectric layer configuration atop one or more electrodes, such as a single-layer dielectric configuration; (2) providing a second region that has a second dielectric layer configuration atop one or more electrodes, such as a two-layer dielectric configuration; (3) optionally, providing a third region that has a third dielectric layer configuration atop one or more electrodes that includes a dielectric layer having a thickness gradient for generating an electrostatic energy gradient; and (4) providing a certain electrowetting voltage value that is a function of the certain respective dielectric layer configuration of the certain respective region of the actuator at which the desired droplet operations are performed.

CONCLUDING REMARKS

The foregoing detailed description of embodiments refers to the accompanying drawings, which illustrate specific embodiments of the invention. Other embodiments having different structures and operations do not depart from the scope of the present invention. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation, as the present invention is defined by the claims as set forth hereinafter.

We claim:

1. A droplet actuator comprising:

a first substrate comprising a first plate and a second substrate comprising a second plate separated first plate by a gap wherein the first plate comprises an electrode configuration comprising electrodes arranged for conducting one or more droplet operations, the electrode configuration comprising:

a first electrode coupled to a voltage source, and first dielectric layer configuration comprising a first dielectric material layered above and along the length of the first electrode, the first dielectric material having a electrostatic energy gradient-establishing variation along the length of the electrode, wherein the droplet actuator is configured such that when voltage is applied to the first electrode, the electrostatic energy gradient is established at a surface of the first substrate along the length of the first electrode which causes a droplet to be transported along the length of the first electrode in a direction established by the energy gradient; and a second electrode coupled to a second voltage source, and a second dielectric layer configuration comprising a second dielectric material layered above the second electrode, wherein the second dielectric layer configuration differs from the first dielectric layer configuration; and wherein the second substrate lacks a dielectric material configured to establish a droplet-transporting energy gradient.

2. The droplet actuator of claim 1 wherein the first electrode is a two terminal electrode composed of a resistive material, such that the first electrode functions as a resistor with a spatial distribution of electric potential along its length.

3. The droplet actuator of claim 1 wherein the first electrode is coupled to a second voltage source.

4. The droplet actuator of claim 3 wherein the first voltage source and the second voltage source are actively applying voltage, and the voltages applied are actively establishing a voltage difference between the first and second voltage sources.

5. The droplet actuator of claim 4 wherein the voltage difference ranges from about >0 volts to about 300 volts.

6. The droplet actuator of claim 1 wherein the first electrostatic energy gradient results from a gradient in thickness of the material layered above the electrode.

7. The droplet actuator of claim 1 wherein the electrostatic energy gradient results from a gradient in dielectric constant of the dielectric material layered above the first electrode.

8. The droplet actuator of claim 1 wherein the electrostatic energy gradient results from a gradient in distance between the first electrode's surface and the surface of the first dielectric layer configuration.

9. The droplet actuator of claim 1 wherein the electrostatic energy gradient is continuous.

10. The droplet actuator of claim 1 wherein the electrostatic energy gradient is discontinuous.

11. The droplet actuator of claim 1 wherein the second dielectric material is layered above and along the length of the electrode, the second dielectric material having a difference in thickness along the length of the electrode, wherein the droplet actuator is configured such that when voltage is applied to the second electrode, an electrostatic energy gradient is established at a surface of the first substrate along the length of the second electrode which causes a droplet to be transported along the length of the second electrode in a direction established by the energy gradient.

12. The droplet actuator of claim 1 wherein the second electrode is a two terminal electrode composed of a resistive material, such that the electrode functions as a resistor with a spatial distribution of electric potential along its length.

13. The droplet actuator of claim 1 wherein the second electrode is coupled to a third voltage source in addition to the second voltage source.

14. The droplet actuator of claim 13 comprising a voltage difference between the second and third voltage sources.

15. The droplet actuator of claim 14 wherein the voltage difference ranges from about >0 volts to about 300 volts.

16. The droplet actuator of claim 1 wherein the second dielectric material layered above the second electrode comprises a difference in thickness comprises a gradient in thickness of the material layered above the electrode.

17. The droplet actuator of claim 1 wherein the second dielectric material layered above the second electrode comprises a gradient in dielectric constant.

18. The droplet actuator of claim 1 wherein the second dielectric material layered above the second electrode comprises a gradient in distance between the second electrode's surface and the surface of the second dielectric layer configuration.

19. The droplet actuator of claim 1 wherein the second dielectric material establishes an electrostatic energy gradient which is continuous.

20. The droplet actuator of claim 1 wherein the second dielectric material establishes an electrostatic energy gradient which is discontinuous.

* * * * *